(12) United States Patent
Martin et al.

(10) Patent No.: US 10,265,175 B2
(45) Date of Patent: Apr. 23, 2019

(54) IMPLANT WITH IMPROVED SURFACE PROPERTIES

(71) Applicant: Ossis Limited, Christchurch (NZ)

(72) Inventors: Madeleine Bess Martin, Christchurch (NZ); John Arthur Calder, Tauranga (NZ)

(73) Assignee: OSSIS LIMITED, Christchurch (NZ)

( * ) Notice: Subject to any disclaimer, the term of this patent is extended or adjusted under 35 U.S.C. 154(b) by 0 days.

(21) Appl. No.: 15/505,095

(22) PCT Filed: Aug. 19, 2015

(86) PCT No.: PCT/NZ2015/050116
§ 371 (c)(1),
(2) Date: Feb. 19, 2017

(87) PCT Pub. No.: WO2016/028171
PCT Pub. Date: Feb. 25, 2016

(65) Prior Publication Data
US 2017/0266008 A1  Sep. 21, 2017

(30) Foreign Application Priority Data

Aug. 19, 2014 (NZ) ........................ 628997

(51) Int. Cl.
*A61F 2/38* (2006.01)
*A61F 2/30* (2006.01)
*A61F 2/36* (2006.01)

(52) U.S. Cl.
CPC ............ *A61F 2/30942* (2013.01); *A61F 2/36* (2013.01); *A61F 2002/30579* (2013.01); *A61F 2002/30736* (2013.01); *A61F 2002/30909* (2013.01)

(58) Field of Classification Search
CPC ............... A61F 2/3662; A61F 2/30907; A61F 2/30724; A61F 2002/30601; A61F 2002/30602; A61F 2002/30579; A61F 2002/30581
See application file for complete search history.

(56) References Cited

U.S. PATENT DOCUMENTS

| 4,936,859 A | 6/1990 | Morscher et al. |
| 2013/0018482 A1* | 1/2013 | Meridew ............. A61F 2/30724 623/23.46 |
| 2013/0211533 A1* | 8/2013 | Fonte ..................... A61L 27/00 623/22.4 |

FOREIGN PATENT DOCUMENTS

| GB | 2495272 | 4/2013 |
| WO | 2012/154534 | 11/2012 |

OTHER PUBLICATIONS

International Search Report for International Application No. PCT/NZ2015/050116, dated Nov. 23, 2015, Applicant, Ossis Limited (7 pages).

* cited by examiner

*Primary Examiner* — Brian Dukert
(74) *Attorney, Agent, or Firm* — Richards Patent Law P.C.

(57) ABSTRACT

This invention relates to and orthopedic implant having an expansion means adapted to increase the external surface area of the implant, the expansion means positioned to correspond to voids or depressions in the anatomy of a patient. Also described are method for the design and manufacture of such implants.

5 Claims, 3 Drawing Sheets

IMPLANT WITH IMPROVED SURFACE PROPERTIES

CROSS-REFERENCE TO RELATED APPLICATIONS

This application is a U.S. National Stage Entry of PCT/NZ2015/050116 filed Aug. 19, 2015, which claims the benefit of priority to New Zealand Patent Application No. 628997 filed Aug. 19, 2014, each of which are incorporated in their entireties by reference.

TECHNICAL FIELD

This invention relates to an orthopaedic implant with regions of expandable surface.

BACKGROUND ART

One of the key factors in successful placement and acceptance of an orthopaedic implant is the osseointegration between a load-bearing implant and the existing patient bone.

Osseointegration involves the formation of a direct interface between an implant and bone, without intervening soft tissue, resulting in a firmly positioned implant that is unlikely to cause any pain or problem to the patient.

In order for effective osseointegration to occur, the outer surface of the implant should contact or nearly contact the surrounding bone tissue in order to encourage the formation of new bone against or preferably within the outer surface of the implant. Any voids or depressions in the patient bone increase the chance of spaces being present between the implant and the surrounding bone, which makes it difficult for osseointegration to occur. This can lead to weakening of the implant and discourage bone growth, as stress is unable to be transferred to the surrounding bone due to the void. As placing a bone under stress promotes growth, such a situation is not optimal.

Patient-specific implants that are designed to contour exactly to a patient's anatomy are known in the art, and are used to optimise the fit of an implant into a patient. These implants are designed and generated using patient information derived from scans, then manufactured into an implant, typically using additive manufacturing.

While these implants go some way to addressing the difficulties associated with curves and depressions within a patients anatomy, in some circumstances it is not possible to shape a patient-specific implant to fill voids, as having protrusions on the implant surface introduces difficulties with locating the implant correctly in the bone. Protrusions can prevent an implant from reaching the desired position, particularly in an area where the void for the implant tapers, for example in the case of a femoral stem implant or in the replacement of the head or stem of any long bone within the body.

OBJECT OF THE INVENTION

It is an object of the invention to provide an implant that is adapted to fill voids and depressions within patient bone.

Alternatively, it is an object of the invention to at least provide the public with a useful choice.

SUMMARY OF THE INVENTION

According to a first embodiment of the invention there is provided an orthopaedic implant, the outer wall of the implant including at least one expansion means adapted to increase the external surface area of the implant, the expansion means positioned to correspond to voids or depressions in the anatomy of a patient.

Preferably, the implant is a patient specific implant, and the location of the expansion means is determined based on patient-specific anatomical information.

In further preferred embodiments the external surface of the implant outer wall includes one or more regions of three dimensional lattice.

More preferably, the expansion means includes one or more regions of three dimensional lattice.

In one preferred embodiment the three dimensional lattice includes one or more rows of three dimensional lattice, wherein the rows of lattice are adjacent, but not connected to each other.

Preferably, the implant wall includes expansion means to allow the surface area of the implant to expand. More preferably the expansion means are located between the rows of three dimensional lattice.

In further preferred embodiments, the three dimensional lattice is expandable.

In preferred embodiments the three dimensional lattice includes bendable struts.

More preferably the lattice includes struts formed with an area of relative weakness along their length such that they bend when in the non-expanded position and straighten or partially straighten when the area is expanded.

Alternatively, the expansion means is an area of the implant wall adapted to move from a first position to a second expanded position using a press mechanism.

Alternatively, the expansion means is an area of the implant wall adapted to move from a first position to a second expanded position using a screw mechanism.

In one preferred embodiment, the expansion means is an area of the implant wall including folds or bends.

More preferably the folds or bends are adapted to allow expansion to occur using a concertina mechanism.

Alternatively, the expansion means is an area of implant wall corresponding to a defect or void, the area of implant wall being only partially connected to the implant using a hinge mechanism, such that the expansion means can be moved about the hinge from a first insertion position inside the outer surface of the implant to a second expanded position extending outwardly from the implant surface.

More preferably the implant includes a means to maintain the hinged expansion means in the second expanded position.

Preferably, the expansion means is integrally formed with the implant.

According to a further embodiment of the invention there is provided a method for the manufacture of an orthopaedic implant, wherein the outer wall of the implant includes at least one expansion means adapted to increase the external surface area of the implant, the expansion means positioned to correspond to predicted voids or depressions in the anatomy of a patient, the method including the steps of;
  a. extracting information regarding bone geometry at a specific anatomical region from stored population data about said bone geometry;
  b. identifying voids or depressions in bone geometry from information of step a);
  c. determining one or more locations on the implant outer wall for forming the expansion means from the information from steps a) and b);

d. designing an implant, the implant including one or more expansion means positioned based on the information from step c);

e. manufacturing implant based on design of step (d) using additive manufacturing techniques.

According to a still further embodiment of the invention, there is provided a method for the manufacture of a patient-specific orthopaedic implant, wherein the outer wall of the implant includes at least one expansion means adapted to increase the external surface area of the implant, the expansion means positioned to correspond to voids or depressions in the anatomy of a patient, the method including the steps of;

a. extracting patient-specific information regarding a patient's bone geometry at a specific anatomical region;

b. identifying voids or depressions in patient's bone geometry from information of step a);

c. determining one or more locations on the implant outer wall for forming the expansion means from the information from steps a) and b);

d. designing a patient-specific implant, the implant including one or more expansion means positioned based on the information from step c);

e. manufacturing implant based on design of step (d) using additive manufacturing techniques.

Preferably, the method of manufacture includes the step of manufacturing one or more regions of three dimensional lattice on the outer surface of the implant.

More preferably, the one or more regions of three dimensional lattice are directly or indirectly connected to the one or more expansion means.

More preferably, the method of manufacture includes the steps of designing and manufacturing the expansion means to include one or more regions of three dimensional lattice.

In one preferred embodiment the method includes the steps of designing and manufacturing the three dimensional lattice to include one or more rows of three dimensional lattice, wherein the rows of lattice are adjacent, but not connected to each other.

Preferably, the method includes the steps of designing and manufacturing the implant wall to include expansion means adapted to allow the surface area of the implant to expand. More preferably the expansion means are located between the rows of three dimensional lattice.

In further preferred embodiments, the method includes the steps of designing and manufacturing expandable three dimensional lattice.

In preferred embodiments the three dimensional lattice includes bendable struts.

More preferably, the method includes the steps of designing and manufacturing lattice that includes struts formed with an area of relative weakness along their length such that they bend when in the non-expanded position and straighten or partially straighten when the area is expanded.

Alternatively, the expansion means is an area of the implant wall adapted to move from a first position to a second expanded position using a press mechanism.

Alternatively, the expansion means is an area of the implant wall adapted to move from a first position to a second expanded position using a screw mechanism.

In one preferred embodiment, the expansion means is an area of the implant wall including folds or bends.

More preferably the folds or bends are adapted to allow expansion to occur using a concertina mechanism.

Alternatively, the expansion means is an area of implant wall corresponding to a defect or void, the area of implant wall being only partially connected to the implant using a hinge mechanism, such that the expansion means can be moved about the hinge from a first insertion position inside the outer surface of the implant to a second expanded position extending outwardly from the implant surface.

More preferably the implant includes the step of designing and manufacturing a means to maintain the hinged expansion means in the second expanded position.

Preferably the method includes, following step d), predicting the loads to be placed on the expansion means and determining the mechanical strength of the expansion means as designed.

More preferably the method includes the step of redesigning the expansion means should the mechanical strength of the expansion means or part thereof fall outside a predetermined acceptable level.

Preferably, the step of load prediction is made using finite element analysis techniques.

According to a further embodiment of the invention there is provided a method for the expansion of a patient-specific orthopaedic implant to fill a void or space in a patient's anatomy, the method including the steps of;

a. locating an implant as described in one or more of the embodiments above in an anatomically correct position in a patient's body as decided by pre-operative planning;

b. actuating the one or more expansion means in the implant wall to extend the outer implant wall to fill the void or pace in the patient's anatomy.

In preferred embodiments of the invention the expansion means is expandable using a concertina mechanism and the step of actuating the one or more expansions means includes the step of applying force to the expansion means from the inside of the implant or surface opposing the outer surface of the implant to extend the folds of the concertina to expand the surface area of the outer surface of the implant to fill the void or space in a patient's anatomy.

In alternative embodiments of the invention the expansion means is expandable using a screw mechanism and the step of actuating the one or more expansions means includes the step of using a tool to screw the expansion means from the inside of or surface opposing the outer surface of the implant to expand the surface area of the outer surface of the implant to fill the void or space in a patient's anatomy.

In further alternative embodiments of the invention the expansion means is expandable using a press mechanism and the step of actuating the one or more expansions means includes the step of applying force to the expansion means from the inside of or surface opposing the outer surface of the implant to push the outer surface of the implant to fill the void or space in a patient's anatomy.

For the purposes of this invention the term "press mechanism" should be taken to mean any mechanism that can be deformed by applying pressure to the mechanism to force a change in shape or size. For example a surface or outer wall of an implant may be formed with a concave shape, which following pressure being applied, will deform outwards to form a convex shape.

Further aspects of the invention, which should be considered in all its novel aspects, will become apparent to those skilled in the art upon reading of the following description which provides at least one example of a practical application of the invention.

DESCRIPTION OF THE DRAWINGS

One or more embodiments of the invention will be described below by way of example only, and without intending to be limiting, with reference to the following drawings, in which.

DETAILED DESCRIPTION OF THE INVENTION

The implants of the current invention disclose implants with expandable regions that enable the outer contours of an orthopaedic implant to be extended once the implant has been positioned within a patient's body. Such expandable regions enable an implant to be designed that optimises the fit of the implant with a specific patient, providing a maximum surface area wherein the implant can mimic the naturally occurring bone contours of the patient.

The orthopaedic implants and methods of the present invention are designed to increase osseointegration with patient bone and cause accretion and strengthening of the existing bone by providing an implant that incorporates surface features that mimic those of healthy bone and/or specific features within a patient bone at a similar location in the body. By incorporating expandable regions into the outer walls of implants, voids that were previously either left empty or packed with bone graft may be filled with a portion of implant wall, preferably incorporating a three dimensional lattice on the outer surface. This brings additional strength to the implant area, improves osseointegration and results in a more stable, better integrated implant.

Such implants are suitable for use in revision, tumour or deformity situations where there are localised bone deficiencies. One use of the implant would be to position a stable osseointegrative shell in patient bone into which a standard, off the shelf implant can be cemented.

The implants and method of the present invention will be discussed in more detail below with reference to acetabular implants and femoral stem shell implants, but may be applied to orthopaedic implants in any area of the body.

Figure 1:
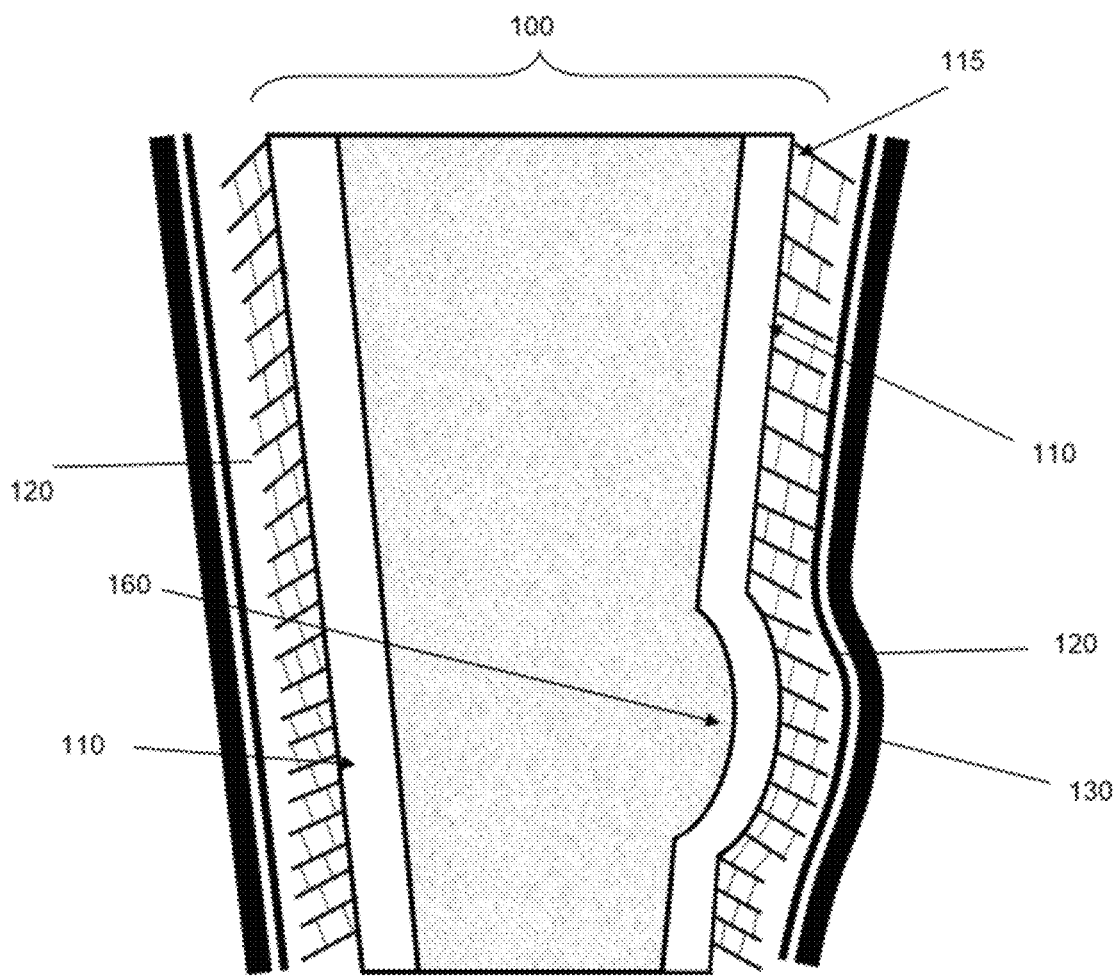
FIG. 1 shows a femoral stem shell implant with an expanded outer surface in one embodiment of the invention.

FIG. 1 shows a section of a femoral stem implant 100 including implant wall 110 with a three dimensional lattice 115 located on the outer surface of wall 110, located in position within a patient's femur, the edges of the femoral cavity defined by regions 120. At location 130 the femoral cavity includes a depression or small void. Implant 100 is manufactured to include a corresponding expandable means 160 located within wall 110, such that when expanded as shown in FIG. 1, the expanded means 160 fills the space 130 in the femoral cavity.

This improves the ability of new bone to grow into three dimensional lattice 115, improving the long term fixation of the implant to existing patient bone.

It should be understood that the femoral stem shell shown here is for diagrammatic purposes only and does not approximate an exact femoral stem shell shape. The exact femoral stem shapes will be preferably be patient specific and may be include expansion means in one or more regions within the stem shell and the shell walls will preferably be contoured to approximate the specific patient's anatomy.

Figure 2:
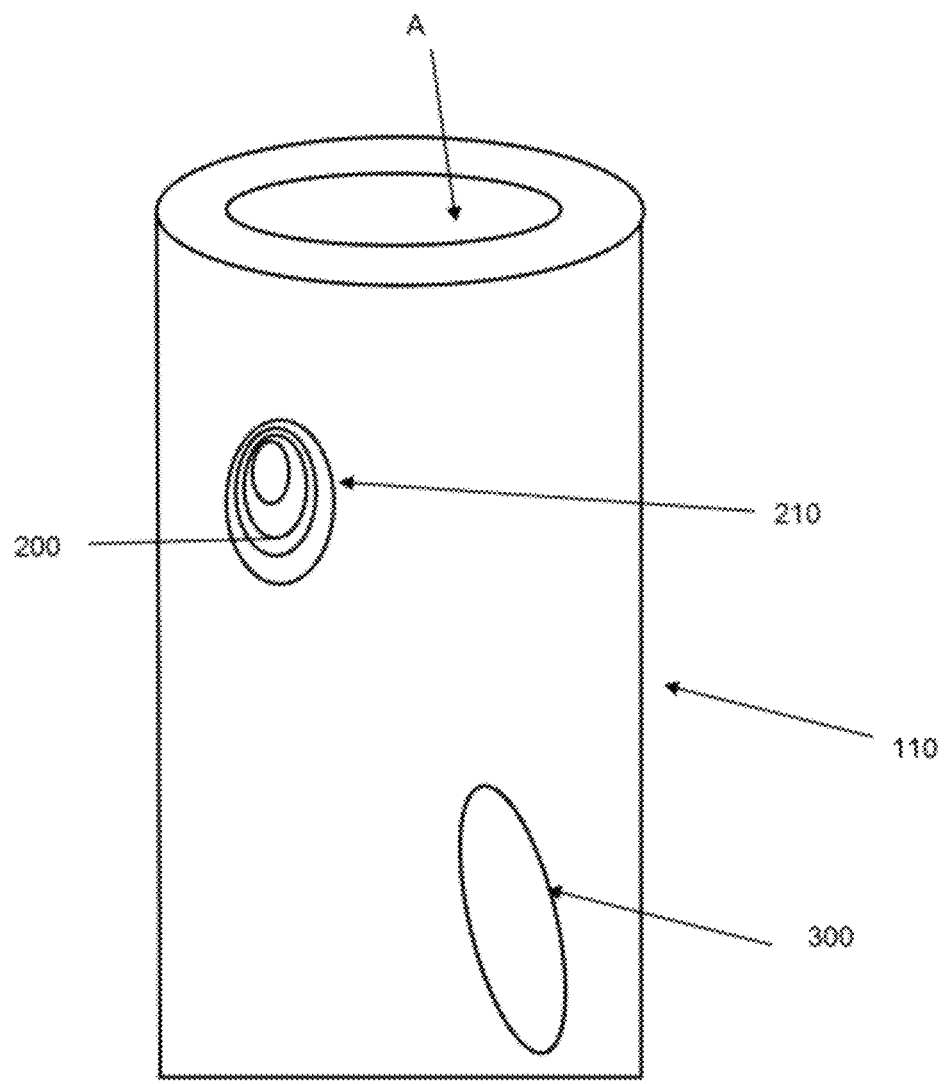
FIG. 2 shows a femoral stem shell implant with two expansion means located on the implant wall in one embodiment of the invention.
Figure 3:
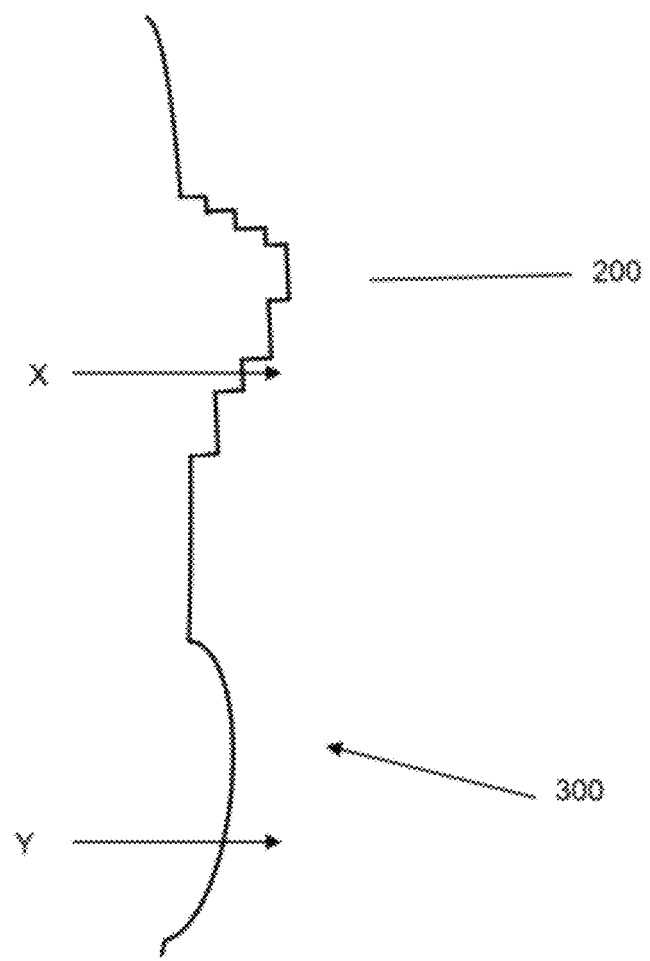
FIG. 3 shows the femoral stem shell implant of FIG. 2, wherein the expansion regions have been expanded to increase the surface area of the implant.

FIGS. 2 and 3 show a femoral stem implant 100 including examples of two separate expansion means 200 and 300 in two embodiments of the invention. As with FIG. 1, expansion means 200 and 300 are located within a wall 110 of implant 110 and are adapted to move from a non-expanded position as shown in FIG. 2 to an expanded position as indicated by the side on view of the implant 100 in FIG. 3. For the purposes of clarity FIGS. 2 and 3 do not show areas of three dimensional lattice on outer wall 110 of implant 100, however this may be present in some embodiments.

Expansion means 200 is adapted to expand using a concertina mechanism. As shown in FIG. 3, when expanded, the surface area of wall 110 increases to enable a void or depression in the patient's anatomy to be filled by the implant wall. When collapsed, expansion means 200 consists of a group of sequentially smaller rings formed by folds that are designed to correspond to a specific shape of a void. In FIG. 2, the void has an off centre apex, such then when expanded a particular shape is formed. Expansion means 200 is expanded by the insertion of a tool inside cavity A of implant 100 applying a force in direction X as shown in FIG. 3. Force X pushes the expandable region into the corresponding void.

The shape of the expanded region can be designed to match a void in a specific patient's anatomy, or may be included in a non-custom implant. In the formation of a custom implant the shape of the expanded region can be determined based on information collated from a population database to determine a best "standard" shape to suit a wide range of patients.

Expansion means 300 shown an alternative embodiment, wherein expansion means 300 is expanded from a first position in FIG. 2 to the expanded position shown in FIG. 3 by means of a press-fit mechanism. When expansion means 300 is unexpanded or depressed it may form a concave depression on the outer surface 110 of implant 100. Following application of a force in direction Y, expansion means 300 may expand outwards from surface 110 to form a convex protrusion that can fill a corresponding void.

The press fit mechanism is the more preferred embodiment of the invention, as the expansion means may be simply activated or extended by the application of force in direction Y. Depending on the shape of region 160, the expansion may occur in a single step, or a number of locations on expansion means 160 may be forced to entirely expand the region.

As with the concertina mechanism described above, the press fit expansion region can be designed to match a void in a specific patient's anatomy, or may be included in a non-custom implant. In the formation of a custom implant the shape of the expanded region can be determined based on information collated from a population database to determine a best "standard" shape to suit a wide range of patients.

In other embodiments (not shown) an expansion means may be moveable from a first non-expanded position to an expended position by a number of other means, such as by the actuation of a screw mechanism that acts to screw the expansion means outward from the surface of an implant.

It should be clear that the expansion means may take any shape as required to fill a corresponding void or depression in a patient bone.

In a preferred embodiment of the invention the expandable region includes three dimensional lattice formed over at least a portion of the outer surface of the implant, including the expansion region. The three dimensional lattice should be of a design such that the lattice has some flexibility in the expansion region to allow it to move from a first non-expanded position to the second expanded position without restricting the movement of the expandable surface due to a rigid structure.

In a first example the three dimensional lattice is formed from an array of interconnected struts that result in a porous mesh. In areas of non-expansion in the implant the struts are typically formed with a substantially uniform cross section or width across the length of the strut. In the area of expansion however, the struts of the mesh in the expansion area are longer than the rest of the mesh, and formed with an area of weakness (or a thin section) along their length such that they bend when in the compacted position and straighten out when the area is expanded.

A mesh containing such a design can be formed with all struts in a particular direction including the bendable feature such that the region is able to expand and contract in a particular direction. Alternatively, all struts or the majority of the struts may have a bendable region, allowing for compression and expansion in any direction. The location, length and design of the bendable struts can be tailored to specifically create properties within the expansion region that are suited to a patient-specific implant. By tailoring the amount of struts in a specific region can bend it is possible to create expandable regions with specific shapes. This can also make it simpler for the surgeon to expand the implant region effectively during the surgical procedure, as the region may be designed to expand only into the correct shape.

It is a key requirement of the lattice to maintain structural and mechanical integrity in order to achieve optimum osseointegration. Any weaknesses in the struts must be suitable to allow bending of the strut, without failing or breaking and this should be taken into consideration with the design of the lattice at the area of expansion.

Altering the materials used in forming the lattice structure may also allow for the creation of regions with different strengths. For example Ti6Al4V, tantalum, cobalt-chrome or other forms of titanium may be used to create lattice with specific regions of flexibility and strength.

In alternative embodiments the lattice itself does not expand, but the surface of the implant expands between areas of lattice. The three dimensional lattice over the expansion area can be formed in rows of lattice that are adjacent each other but not touching. Between the rows of lattice the surface of the implant includes folds, bends or other means to allow the surface area of the implant to expand and potentially contract. When the expansion region is pushed out, these folds or bends expand so that expansion of the region results in rows of lattice having wider gaps between them than were present in the non-expanded position.

In still further embodiments the expansion means may be an area of implant wall corresponding to a defect or void, the area of implant wall being only partially connected to the implant using a hinge mechanism, such that the expansion means can be moved about the hinge from a first insertion position inside the outer surface of the implant to a second expanded position extending outwardly from the implant surface. Using this design the outer implant wall will include a void corresponding to the expansion means, with the expansion means being connected at one edge of the void by a hinge mechanism. As the implant is being inserted into the patient the expansion means is retained within the implant to prevent it being an obstacle to insertion. Once the implant is in position, the expansion means is pivoted around the hinge mechanism until the expansion means is pushed outwardly from the outer surface of the implant into the corresponding to the void in the patient.

This design may also include a mechanism to retain the expansion means in the extended position and prevent movement in the reverse direction around the hinge. Such a mechanism may include a clip fit mechanism, hook, catch or lock and key means that will retain the expansion means in the extended position.

As would be understood by a person skilled in the art the expansion area may be designed with a one way expansion region, which allows the expanded region to stay expanded permanently. In other embodiments the expansion region may include means to withdraw the expansion region should the implant need to be removed during a revision procedure. This feature would be particularly suitable for an implant where the internal region of the expansion area can be reached by the surgeon, allowing a hook or gripping means to be located within the expansion region for example to withdraw it back to the non-expanded position.

Following expansion of the one or more expansion means within an implant, the expansion means have the further advantage of acting as anchors, further securing the implant in position. This is particularly useful in the femoral region, and in particular in a femoral stem shell, as stress introduced from the hip encourages movement of the implant in a downward direction, commonly known as subsidence which can result in shortening of the leg. Expansion means protruding from the implant surface will go some way to alleviating this downward movement.

In manufacturing the implant of the present invention, information regarding the anatomy of a patient at an implant site, including the identification of any voids or depressions surrounding the implant region is gathered and a model of the implant is developed to include expansion means positioned within the wall of the implant to allow the implant, once in position, to be expanded to fill the depressions or voids. Such imaging used to determine the patient anatomy may be in the form of CT-scans, X-rays, MRI scans or radiography techniques for example.

In a non-custom implant, expansion means may be included within the implant to enable the expansion of an implant wall in regions where a void or depression is common across a large portion of the affected population.

For custom or patient-specific implants the desired anatomical shape of the implant will be determined using analysis of scanned patient imagery to optimise the contact between the implant and bone when located within a patient. Regions for the location of expansion means can then be identified and incorporated into the implant design. In some circumstances protrusions on the outer surface of the implant may be solidly formed within the implant surface, particularly if the location of the protrusion on the implant will not introduce any additional difficulties inserting the implant into position.

In circumstances where having a protrusion located on the outer surface of the implant will prevent or severely obstruct the correct seating of the implant within the patient, an expansion means will be more appropriate. This will allow the implant to be correctly and relatively easily seated in position before expanding the implant surface area to fill the voids.

As well as determining the location and shape of the expansion means to be included within an implant, the surface structure at the site of the expansion means will also need to be established. In preferred embodiments a three dimensional lattice is integrally formed on the surface of the implant, with the preferred three dimensional lattice being a trabecular mesh or a custom designed lattice formed from plates and rods. In some circumstances a roughened surface may be preferable.

As would be clear to a person skilled in the art, the type of surface selected will need to be determined in conjunction with the type of expansion means used. For example if a relatively porous mesh is required with a large unit cell size, an expansion means that operates using a press mechanism may be more suitable than an expansion means operable using a concertina mechanism, as the reduced amount of fold or creases in the implant structure of a press mechanism would be less disruptive to the lattice structure.

Once the required measurements and analysis of specific requirements in terms of void location, type and position of expansion means and surface materials by the orthopaedic expert have been conducted, a 3D model is developed.

The 3D model can be tested to determine the performance of the expansion region under the predicted stresses.

For example, when creating a lattice having bendable struts with areas smaller cross section it is possible to ensure the loads placed on the lattice during the expansion process and once in position in the patient, do not exceed the mechanical capabilities of the lattice. Using computer modelling and finite element analysis the predicted loads of the lattice when moving between the non-extended and extended positions can be determined during the design phase to ensure the flexible struts can withstand the bending forces. Variations to the mesh design can then be made as needed until a structurally sound design is created. These variations may be in the type of material used or the design of the lattice.

The model is then used to manufacture the patient-specific implant using additive manufacturing techniques, preferably EBM manufacturing. Following manufacture of the implant, the implant is then surface finished if necessary, cleaned and/or sterilised before being provided to a hospital or surgical professional for use.

In use, the implants of the present invention are particularly suitable for implants that include an internal cavity so that any expansion means can be activated from the inner walls of the implant, for example a femoral stem shell implant, or implants that have an accessible inner wall once the implant is in position, for example an acetabular implant. The expansion means of the present invention may also be applied to dental implants, implants for the lower femur, upper and lower tibia and around the shoulder joint for example.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

We claim:

1. A method for the manufacture of an orthopaedic femoral shell implant, wherein the outer wall of the femoral shell implant includes at least one expansion means adapted to increase the external surface area of the implant at one or more discrete regions on the outer wall of the femoral shell, the expansion means positioned on the outer wall of the femoral shell such that, in use, it corresponds with specific, predetermined voids or depressions in the anatomy of a patient, the method including the steps of;
    a. extracting information regarding bone geometry at a specific anatomical region from stored population data about said bone geometry;
    b. identifying voids or depressions in bone geometry from information of step a);
    c. determining one or more locations on the implant outer wall for forming the expansion means from the information from steps a) and b);
    d. designing an implant, the implant including one or more expansion means positioned based on the information from step c);
    e. manufacturing implant based on design of step (d) using additive manufacturing techniques.

2. A method for the manufacture of an orthopaedic femoral shell implant, wherein the outer wall of the femoral shell implant includes at least one expansion means adapted to increase the external surface area of the implant at one or more discrete regions on the outer wall of the femoral shell, the expansion means positioned on the outer wall of the femoral shell such that, in use, it corresponds with specific, predetermined voids or depressions in the anatomy of a patient, the method including the steps of;
    f. extracting patient-specific information regarding a patient's bone geometry at a specific anatomical region;
    g. identifying voids or depressions in patient's bone geometry from information of step a);
    h. determining one or more locations on the implant outer wall for forming the expansion means from the information from steps a) and b);
    i. designing a patient-specific implant, the implant including one or more expansion means positioned based on the information from step c);
    j. manufacturing implant based on design of step (d) using additive manufacturing techniques.

3. The method of claim 2, wherein the method includes the step of manufacturing one or more regions of three dimensional lattice on the outer surface of the implant.

4. The method as claimed in claim 2, wherein the method includes, following step d), predicting the loads to be placed on the expansion means and determining the mechanical strength of the expansion means as designed.

5. The method of claim 4, wherein the method includes the step of redesigning the expansion means should the mechanical strength of the expansion means or part thereof fall outside a pre-determined acceptable level.

* * * * *